US007072714B2

(12) United States Patent
Busch et al.

(10) Patent No.: US 7,072,714 B2
(45) Date of Patent: Jul. 4, 2006

(54) PACEMAKER CONTROL DEPENDENT ON NATURAL AV CONDUCTION OR PVC/VES DETECTION

(75) Inventors: Ulrich Busch, Berlin (DE); Max Schaldach, deceased, late of Erlangen (DE); by Max Schaldach, Jr., legal representative, Berlin (DE)

(73) Assignee: Biotronik Mess-und Therapiegeraete GmbH & Co. Ingenieurbuero, Berlin (DE)

( * ) Notice: Subject to any disclaimer, the term of this patent is extended or adjusted under 35 U.S.C. 154(b) by 601 days.

(21) Appl. No.: 10/200,568

(22) Filed: Jul. 19, 2002

(65) Prior Publication Data

US 2003/0023281 A1 Jan. 30, 2003

(30) Foreign Application Priority Data

Jul. 19, 2001 (DE) ............................... 101 36 641

(51) Int. Cl.
*A61N 1/362* (2006.01)
(52) U.S. Cl. ...................................................... 607/14
(58) Field of Classification Search ................ 607/4, 607/9, 14
See application file for complete search history.

(56) References Cited

U.S. PATENT DOCUMENTS

| 4,407,287 A | * | 10/1983 | Herpers .......................... 607/9 |
| 4,788,980 A | | 12/1988 | Mann |
| 5,074,308 A | | 12/1991 | Sholder |
| 5,097,832 A | | 3/1992 | Buchanan |
| 5,228,438 A | | 7/1993 | Buchanan |

(Continued)

FOREIGN PATENT DOCUMENTS

DE 691 17 410 T2 10/1996

(Continued)

*Primary Examiner*—Robert E. Pezzuto
*Assistant Examiner*—Kristen Mullen
(74) *Attorney, Agent, or Firm*—Hahn Loeser & Parks LLP (57) ABSTRACT

A dual-chamber cardiac pacemaker comprising an atrial detection unit which is adapted to detect electrical signals in the atrium of a heart as atrial sense events, a ventricular detection unit which is adapted to detect electrical signals of a ventricle of the heart as ventricular sense events, a stimulation unit which is adapted at least to trigger the delivery of electrical pulses to the ventricle as ventricular stimulation events, and a control unit which is connected to the atrial and the ventricular detection units and the stimulation unit and adapted to control triggering of the delivery of pulses in dependence on the atrial detection unit and the ventricular detection unit in such a way that pulse delivery to the ventricle is triggered after the expiry of an AV time after detection of an atrial sense or stimulation event if prior to expiry of the AV time no ventricular sense event is detected by the ventricular detection unit, wherein the control unit is further adapted to divide ventricular sense events into at least two categories of which a first category concerns ventricular sense events to be associated with natural stimulus conduction from the atrium to the ventricle while a second category concerns ventricular sense events to be associated with ventricular extrasystoles or premature ventricular contractions (PVC) and control of the cardiac pacemaker is differentiated in accordance with whether a ventricular sense event is or is not associated with the first category, characterized in that for the control of triggering of pulse delivery an AV monitoring interval is provided in such a way that the AV monitoring interval is triggered by each atrial sense event which is outside an atrial refractory time, wherein the cardiac pacemaker is adapted to associate ventricular events occurring within the AV monitoring interval to the first category.

20 Claims, 2 Drawing Sheets

U.S. PATENT DOCUMENTS

| | | | |
|---|---|---|---|
| 5,312,451 A * | 5/1994 | Limousin et al. | 607/15 |
| 5,814,077 A * | 9/1998 | Sholder et al. | 607/9 |
| 6,029,087 A * | 2/2000 | Wohlgemuth | 607/9 |
| 6,192,274 B1 | 2/2001 | Worzewski | |
| 6,311,088 B1 * | 10/2001 | Betzold et al. | 607/14 |
| 6,609,028 B1 * | 8/2003 | Struble | 607/14 |
| 6,671,548 B1 * | 12/2003 | Mouchawar et al. | 607/14 |

FOREIGN PATENT DOCUMENTS

| | | |
|---|---|---|
| DE | 692 26 921 T2 | 5/1999 |
| DE | 198 27 807 A1 | 12/1999 |
| DE | 198 59 652 A1 | 6/2000 |

* cited by examiner

PACEMAKER CONTROL DEPENDENT ON NATURAL AV CONDUCTION OR PVC/VES DETECTION

The invention concerns a dual-chamber cardiac pacemaker comprising an atrial detection unit which is adapted to detect electrical signals in the atrium of a heart as an atrial sense event, a ventricular detection unit which is adapted to detect electrical signals of a ventricle of the heart as a ventricular sense event, a stimulation unit which is adapted at least to trigger the delivery of electrical pulses to the ventricle as ventricular stimulation events, and a control unit which is connected to the atrial and the ventricular detection units and the stimulation unit and adapted to control triggering of the delivery of pulses in dependence on the atrial detection unit and the ventricular detection unit in such a way that pulse delivery to the ventricle is triggered after the expiry of an AV time after detection of an atrial sense or stimulation event if prior to expiry of the AV time no ventricular sense event is detected by the ventricular detection unit, wherein the control unit is further adapted to divide ventricular sense events into at least two categories of which a first category concerns ventricular sense events to be associated with natural stimulus conduction from the atrium to the ventricle while a second category concerns ventricular sense events to be associated with ventricular extrasystoles or premature ventricular contractions (PVC) and control of the cardiac pacemaker is differentiated in accordance with whether a ventricular sense event is or is not associated with the first category.

BACKGROUND OF THE ART

Cardiac pacemakers are usually identified by three letters, of which the first letter identifies the stimulated chamber, the second letter identifies the perceiving chamber (sensing) and the third letter identifies a pacemaker operating mode. The present invention primarily concerns VDD or DDD pacemakers. VDD pacemakers are suitable for stimulating the ventricle of a heart, recording electrical signals both in the ventricle and also in the atrium, and operating both in an inhibiting and also in a triggered mode. DDD pacemakers are additionally capable of also stimulating the atrium of a heart.

Such pacemakers usually involve an atrial refractory time in which electrical signals in the atrium of a heart are either not detected at all or detected signals are not subjected to further processing. Typical signals to be detected, both in the atrium and also in the ventricle of a heart, are atrial or ventricular contractions respectively of the heart, which involve depolarization of the cardiac tissue, which is electrically detectable.

In response to a detected and processed electrical signal in the atrium of a heart, an AV time is usually triggered, at the end of which an electrical stimulation pulse is delivered to the ventricle of the heart if natural contraction of the ventricle is not detected during the AV time.

The time co-ordination of an atrial contraction which is followed by a ventricular contraction is of great significance in regard to hemodynamic efficiency, that is to say the pump efficiency of a heart. Firstly there is a contraction of the atrium which is followed at a given distance by a contraction of a ventricle. After a further time, the VA time, a contraction of the atrium is again due, which is followed after a further AV time again by a contraction of the ventricle, and so forth.

In regard to stimulation in particular of the ventricle, it is necessary to avoid that it does not excessively quickly follow a preceding natural or stimulated contraction of the ventricle as otherwise by virtue of electrical stimulus conduction in the cardiac tissue (myocardium), fibrillation of the ventricle can occur, which results in failure of the pump activity of the heart and can end in death if it is not terminated in good time.

It is further possible for ventricular stimulation events or also natural contractions of the ventricle to be perceived by way of an electrical remote field action in the atrium as electrical signals. Such remote field perception can also result in pacemaker-induced tachycardia.

Finally there can also be retrograde (rearward directed) stimulus conduction from the ventricle to the atrium, which results in premature contraction of the atrium (PAC: premature atrial contraction). If a cardiac pacemaker starts the AV interval by virtue of such a premature atrial contraction and at the end thereof triggers ventricular stimulation, that in turn can result in a further PAC so that the situation then involves pacemaker-induced tachycardia, an excessively increased heart rate.

In order to prevent this, pacemakers usually have a postventricular atrial refractory period (PVARP=Postventricular Atrial Refractory Period). That interval is triggered after a ventricular stimulation event and has the effect that atrial sense events perceived during the PVARP interval are not subjected to further processing for triggering an AV interval. It is known for the PVARP interval to be prolonged after premature ventricular contractions (PVC) or ventricular extrasystoles (VES) in order to avoid pacemaker-induced tachycardia (PMT).

It is possible that natural atrial events are not perceived in particular during a prolonged PVARP. The consequence is that a natural ventricular contraction which follows a non-perceived atrial contraction is perceived not as a natural ventricular contraction but as a ventricular extrasystole and so forth. That phenomenon is known as VES-lockin. VES-lockin can occur both in the VDD mode of operation and also in the DDD mode of operation in the case of pacemakers with a conventional atrial refractory time concept (relatively long PVARP), predominantly at relatively high stimulation rates, if a patient at least temporarily has a relatively slow overconduction of atrial stimuli to the ventricle (AV-overconduction).

A VES-lockin occurs if a premature atrial sense event occurs in an atrial refractory time after a ventricular event, for example in the case of:

premature atrial contractions with sinus node reset during PVARP after a ventricular stimulation event premature atrial contraction with sinus node reset during PVARP after a ventricular sense event premature or regular atrial contraction during a prolonged PVARP after a premature ventricular contraction (the above-depicted case)

if a pacemaker is in the Wenckebach condition in which ventricular stimulation does not occur at the end of the AV interval if at that moment the "upper tracking interval" started with all ventricular sense and stimulation events is not yet concluded but ventricular stimulation is displaced to the end of the upper tracking interval. Here, by virtue of the frequent asynchronicity of atrial and ventricular events, it is possible that a regular atrial sense event occurs in the PVARP (postventricular atrial refractory time) after ventricular stimulation and is (slowly) naturally overconducted. Such ventricular contraction which is based on natural overduction is then classified as ventricular extrasystoles VES.

Besides the specified sources of VES-lockin there are others.

In connection with the prevention of pacemaker-induced tachycardias (PMT) and the prolongation, which serves for that purpose, of the PVARP after a ventricular extrasystole, it happens that a premature atrial contraction or an atrial sense event in the heart is overconducted slowly from the atrium to the ventricle and, in the ventricle, after expiry of the overconduction time provided in the pacemaker, causes ventricular depolarization and contraction of the ventricle, which is then classified by the pacemaker as a ventricular extrasystole. That in turn results in a prolongation of the PVARP.

The next antegrade excitation of the atrium occurs in the prolonged PVARP and, due to natural stimulus conduction from the atrium to the ventricle, triggers the next contraction of the ventricle which is again classified as a ventricular extrasystole. That behavior on the part of the cardiac pacemaker is represented outwardly as a temporary loss of detection of atrial events, atrial sensing.

From the point of view of the patient, longer AV times signify a worsening in ventricle filling as the valves between the atrium and the ventricle close prematurely. That is problematical in the case of some patients. In addition depolarization of the atrium (P-wave) at higher frequencies can occur in a ventricular systole, with the consequence that patients suffer from atrium blockages involve a potential fibrillation risk, as in the case of a pacemaker syndrome. Such a VES-lockin is only terminated when the spontaneous (natural) atrial interval is longer than the PQ interval which extends from an atrial depolarization (P-wave) to a ventricular depolarization (Q-peak), plus the PVARP, or if a main timer of a cardiac pacemaker, which is started with a ventricular extrasystole, expires prior to the next ventricular sense event.

The object of the present invention is to provide as extensive a remedy as possible in respect of the above-depicted problems.

SUMMARY OF THE INVENTION

In accordance with the invention that object is attained by a dual-chamber cardiac pacemaker of the kind set forth in the opening part of this specification, in which an AV monitoring interval is provided for control of triggering of pulse delivery in such a way that the AV monitoring interval is triggered by each atrial sense event which is outside an atrial refractory time, wherein the cardiac pacemaker is adapted to associate ventricular events occurring within the AV monitoring interval to the first category (ventricular contraction based on natural stimulus conduction).

An aspect which is independent thereof but which is basically synergistic in effect provides that for control of triggering of pulse delivery a remote field protection interval and a PMT protection interval are provided in such a way that the remote field protection interval is triggered by each ventricular stimulation event and by each ventricular sense event detected by the ventricular detection unit, wherein the remote field protection interval is such in respect of its time duration that an atrial sense event as a result of a remote field effect of a ventricular event occurs in the remote field protection interval and wherein the effect of the remote field protection interval is that atrial events detected by the atrial detection unit during the remote field protection interval remain disregarded for triggering of pulse delivery by the stimulation unit so that triggering of pulse delivery does not occur after an atrial sense event as a consequence of cross-sensing or remote field detection of ventricular events, and in such a way that the PMT protection interval is triggered by each ventricular stimulation event and by each ventricular sense event detected by the ventricular detection unit if said ventricular event was detected outside a predetermined AV time or outside an AV monitoring interval, wherein if the PMT protection interval were triggered it adjoins the respective remote field protection interval and prolongs same and wherein the effect of the PMT protection interval is that atrial events detected by the atrial detection unit during the PMT protection interval remain disregarded for triggering of pulse delivery by the stimulation unit so that triggering of pulse delivery as a consequence of an atrial event which goes back to retrograde stimulus conduction from the ventricle to the atrium does not occur.

The concept of the conventional atrial refractory time which is intended so-to-speak to protect from atrial sense events due to the remote field effect of ventricular events and retrograde stimulus conduction from the ventricle to the atrium is thus embodied in the cardiac pacemaker according to the invention on the one hand by differentiation of the atrial refractory time following a ventricular event into a remote field protection interval and a subsequent PMT protection interval. In addition the AV monitoring interval is re-introduced, which permits improved classification of ventricular events due to natural stimulus conduction on the one hand and PVCs and VES on the other hand. The remote field protection interval starts with each non-refractory ventricular event. It is precisely of such a length that the atrium is adequately protected from a remote field effect of a ventriculating event. Atrial events within the remote field protection interval remain disregarded in terms of further pacemaker control.

In contrast the PMT protection interval starts exclusively after ventricular stimulation events or such sense events which are outside the AV time or outside the AV monitoring interval, that is to say only after ventricular stimulation events and such ventricular sense events which are attributed to the second category and categorized correspondingly as VES or PVC. During the PMT protection interval, the situation involves preventing retrograde stimulus conductions from the ventricle to the atrium starting AV overconduction of the stimuli from the atrium to the ventricle or being able to reset a main timer of the cardiac pacemaker. Atrial sense events within the PMT protection interval and outside the atrial refractory time however are perceived as sense events and subjected to further processing for further cardiac pacemaker control.

The AV monitoring interval which has already been referred to above and which is also to be provided independently of the remote field protection interval and the PMT protection interval is started with all atrial sense events outside an atrial refractory time and—if present—the remote field protection interval. All depolarization effects which are due both to antegrade stimulus conduction and also retrograde stimulus conduction and also those in a PMT protection interval start the AV monitoring interval. The AV monitoring interval is cancelled again by ventricular stimulation events and ventricular sense events of the first category (due to natural stimulus overconduction).

In a preferred cardiac pacemaker there are provided both an atrial monitoring interval and also a remote field protection interval and a PMT protection interval. If, in such a cardiac pacemaker, atrial depolarization, that is to say an atrial sense event, occurs in the PMT protection interval, then the next ventricular event, within the AV monitoring interval, is classified as a natural ventricular sense event in the first category and not as usual as PVC or VES. Such a ventricular sense event in the first category in contrast to a PVC or a VES does not start a PMT protection interval and the next atrial sense event is detected as an atrial sense event which is to be subjected to further processing for control purposes and can start an AV overconduction. The above-described VES-lockin phenomenon is prevented in that way.

As the AV monitoring interval is started with all atrial sense events outside the atrial refractory time in the Wenckebach mode of operation ventricular perception which occurs within the upper tracking interval and outside the AV interval is interpreted as a regular ventricular sense event and not as a VES as long as the AV monitoring interval is still going on. That here too prevents VES-lockin.

Advantageously a cardiac pacemaker in which there is an AV monitoring interval has one or more of the following features, irrespective of whether the cardiac pacemaker also has a remote field protection interval or a PMT protection interval:

A postventricular atrial refractory time (PVARP) is prolonged if a ventricular sense event is to be attributed to the second category and is left unprolonged if the ventricular sense event is to be attributed to the first category.

The cardiac pacemaker and in particular the control unit thereof is adapted, in the case of ventricular sense events occurring within the AV monitoring interval, to start a VA interval which is terminated prematurely if an atrial sense event occurs prior to the expiry thereof. In that respect this cardiac pacemaker and in particular the control unit thereof are preferably so designed that with an atrial sense event it starts an AA interval which is prematurely concluded if a ventricular sense event occurs within the AV monitoring interval and the VA interval is started or if a atrial sense event occurs prior to expiry of the AA interval. In connection with these preferred embodiments, it is particularly preferable to provide a cardiac pacemaker having an atrial stimulation unit which is adapted to trigger the delivery of electrical pulses to the atrium as atrial stimulation events, in which respect the cardiac pacemaker and in particular the control unit thereof is adapted to trigger the delivery of an atrial stimulation pulse with the expiry of the VA interval or the AA interval if the VA interval or the AA interval are not prematurely concluded.

BRIEF DESCRIPTION OF THE DRAWINGS

The invention will now be described in greater detail by means of an embodiment with reference to the Figures in which.

DETAILED DESCRIPTION OF A PREFERRED EMBODIMENT

Figure 1:
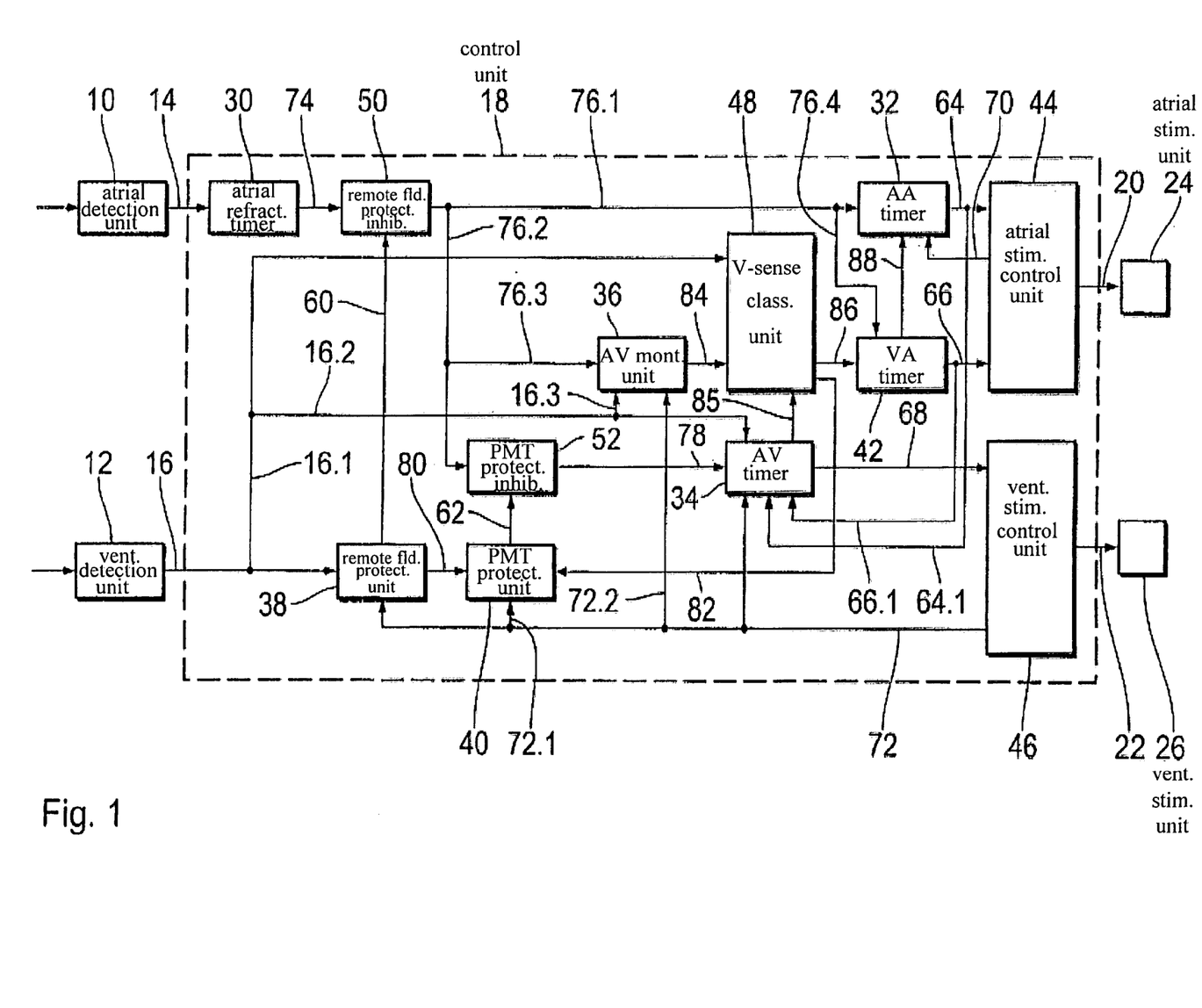
FIG. 1 shows a schematic block circuit diagram of the control of a cardiac pacemaker of the kind according to the invention.

The essential components of the block circuit diagram illustrated in FIG. 1 are an atrial detection unit 10 and a ventricular detection unit 12. In operation of a cardiac pacemaker the detection units 10 and 12 are connected to electrodes in the atrium and in the ventricle respectively of a heart and are adapted to record electrical signals characterizing atrial and ventricular depolarization respectively and to process same and so deliver corresponding control signals if atrial or ventricular depolarization occurs. Those control signals are transmitted by way of signal lines 14 and 16 respectively to a control unit 18. The signals are subjected to processing within the control unit 18. After expiry of the respective signal processing procedure the control unit 18, by way of control lines 20 and 22, delivers control signals to an atrial stimulation unit 24 and a ventricular stimulation unit 26 respectively. The stimulation units 24 and 26 are connected to electrodes arranged in the atrium and the ventricle of the heart respectively and are suitably adapted to deliver electrical pulses to the myocardium of the atrium or the ventricle by way of those electrodes and in that way to stimulate a contraction of the atrium or ventricle respectively.

The control unit 18 is now to be described hereinafter.

First of all it should be noted that a control unit of a cardiac pacemaker can have further features, over and above the features of the control unit 18. For the sake of simplicity the control unit 18 shown in FIG. 1 omits all the functional units which serve for example for checking stimulation success, so-called capture control, as well as functional units for detecting statistical or medical facts of the patient.

Essential units of the control unit 18 are timers, more specifically an atrial refractory time timer 30, an AA timer (maintimer) 32, an AV timer 34, an AV monitoring unit 36, a remote field protection unit 38, a PMT protection unit 40 and a VA timer 42. Besides those timers, there are also an atrial stimulation control unit 44 and a ventricular stimulation control unit 46. Added to these there are a V-sense classification unit 48 and a remote field protection inhibitor 50 as well as a PMT protection inhibitor 52.

What is common to all timers 30 through 42 is that they start a respective time interval due to a triggering control signal and, depending on the respective nature of the timer, during that time interval or with the expiry of the respective time interval, output signals or suppress the transmission of signals.

The timers 32 through 42 can also be reset by way of reset signals.

The two inhibitors 50 and 52 are respectively connected by way of a control line 60 and 62 to a respective timer, more specifically on the one hand the remote field protection unit 38 and on the other hand the PMT protection unit 40. The inhibitors 50 and 52 have the property of interrupting the transmission of signals as long as a corresponding signal is applied by way of the control lines 60 and 62 respectively.

The two stimulation control units 44 and 46 are so designed that on the one hand in response to corresponding control signals applied to control lines 64, 66 or 68, they output control output signals to the stimulation units 24 and 26 respectively by way of the control lines 20 and 22 and in that way trigger stimulation of the atrium or the ventricle respectively. The stimulation control units 44 and 46 further include capture control units (not shown) which are adapted to produce a signal if stimulation of the atrium or the ventricle by way of the stimulation unit 24 or 26 respectively was successful. In that case the stimulation control units 44 and 46 respectively output signals by way of control return lines 70 and 72.

The co-operation of the above-mentioned units and the control lines which have not been referred to previously will now be described, starting from the occurrence of an atrial sense event.

An atrial sense event is detected by the atrial detection unit 10 which thereupon delivers a control signal to the atrial refractory time timer 30 by way of the control line 14. In the timer an atrial refractory interval is now started and at the same time an output signal is transmitted by way of a control line 74 and through the remote field protection unit 50 by way of control lines 76.1, 76.2 and 76.3 to the AA timer 32, the AV monitoring unit 36 and through the PMT protection inhibitor 52 and by way of the control line 78 to the AV interval timer 34.

The AA timer, the AV monitoring unit 36 and the AV interval timer 34 are started in that way by an atrial sense event.

As long as the atrial refractory time interval of the atrial refractory time timer 30 is running, a signal which is applied to the control line 14 and which characterizes an atrial sense event is not being transmitted. An atrial sense event which triggers the atrial refractory time is transmitted by way of the control line 74 but only reaches the control lines 76.1, 76.2 and 76.3 if no corresponding control signal is applied to the remote field protection inhibitor 50 by way of the control line 60. In the same way a signal characterizing an atrial sense event is transmitted to the control line 78 by the control line 76.2 and thus the AV interval timer 34 is triggered, only if the PMT protection inhibitor 52 is not blocked on the basis of a blocking signal applied to the control line 62.

The remote field protection interval timer 38 is triggered when a signal characterizing a ventricular sense event is received by way of the control line 16 or a signal characterizing a ventricular stimulation event is received by way of the control return line 72. In that case a remote field protection interval is started, during which a blocking signal is delivered to the remote field protection inhibitor 50 by way of the control line 60 so that an atrial sense signal which is possibly applied to the control line 74 is not transmitted to the control line 76.1.

The PMT protection interval timer 40 is started after ventricular stimulation events with the expiry of the remote field protection interval by a signal by way of a control line 80 if the remote field protection interval was triggered by a ventricular stimulation event, that is to say a control signal was delivered by way of the control line 72. The remote field protection interval is thus only triggered if in the predetermined time interval firstly a signal 72 arrives at the PMT protection interval unit 40 by way of the control line 72 and then a signal arrives by way of the control line 80.

The PMT protection interval timer 40 is also started after the occurrence of ventricular extrasystoles or premature ventricular contractions with the expiry of the remote field protection interval, also by a signal by way of the control line 80, if a control signal arrives by way of a control line 82 after triggering of the corresponding remote field protection interval. That control signal by way of the control line 82 characterizes the ventricular event which triggers the remote field protection interval and which thus starts the remote field protection timer 38, as a VES or a PVC. The signal by way of the control line 82 originates from the V-sense classification unit 48.

Accordingly each atrial sense event which does not occur within intervals which have already started such as the atrial refractory time, the remote field protection interval and the PMT protection interval, starts the AV interval timer 34 as in those cases the atrial refractory time timer 30, the remote field protection inhibitor 50 and the PMT protection inhibitor 52 were not blocked. If the AV interval timer 34 is started by a control signal characterizing an atrial sense event, by way of the control line 78, an AV interval begins, which, with its duration, specifies when at the latest a ventricular contraction should follow an atrial contraction, so as to afford effective pumping efficiency of the heart.

The AV interval timer 34 is started not only by spontaneous atrial events, that is to say atrial sense events, by way of the control line 78, but also with the delivery of an atrial stimulation pulse after the expiry of a further AA interval discussed hereinafter, or a VA interval. For that purpose the AV interval timer 34 is connected by way of control lines 64.1 and 66.1 to the output of the corresponding AA timer 32 and the output of the VA timer 42 respectively.

If a ventricular sense event is detected by the ventricular detection unit 12 within the AV interval, the AV interval timer 34 receives a signal by way of the control lines 16, 16.1 and 16.2. The AV interval timer is reset by such a control signal by way of the line 16.2.

If the AV interval timer 34 does not receive a control signal by way of the line 16.2 during a running AV interval, it is not reset and with the expiry of the predetermined AV interval outputs a control signal by way of the control line 68, with which the ventricular stimulation control unit 46 is caused to start the ventricular stimulation unit 26. In the case of successful stimulation of the ventricle the ventricular stimulation control unit 46 delivers by way of the control return line 72 to the AV interval timer 34 a signal with which the control signal triggering corresponding stimulation is cancelled on the control line 68.

A particularity of the control unit 18 lies in the AV monitoring unit 36 and the interplay thereof with the V-sense classification unit 48. The AV monitoring unit 36 starts an AV monitoring interval with each signal arriving by way of the control line 76.3 and characterizing an atrial sense event, outside the atrial refractory time and the remote field protection interval. During the duration of the AV monitoring interval which is started in that way, the AV monitoring unit 36 delivers a signal to the V-sense classification unit 48 by way of a control line 84.

Besides the control signal from the AV monitoring unit 36 by way of the control line 84 the V-sense classification unit 48 also receives signals delivered by the ventricular detection unit 12 in the case of detection of ventricular sense events. If the V-sense classification unit 48 receives such a signal characterizing a ventricular sense event by way of the line 16.1 while at the same time an output signal of the AV monitoring unit 36 is applied on the control line 84—if therefore the ventricular sense event is in the AV monitoring interval—then the V-sense classification unit 48 delivers signals to the PMT protection interval timer 40 and the VA interval timer 42 respectively by way of the control lines 82 and 86.

The AV monitoring unit 36 is reset by each ventricular sense or stimulation event, that is to say the respectively corresponding AV monitoring interval is broken off. For that purpose the AV monitoring unit receives by way of a control line 16.3 a signal characterizing a ventricular sense event while a signal characterizing successful ventricular stimulation arrives by way of a control line 72.2. Accordingly signals by way of the control lines 16.3 or 72.2 respectively cause a reset of the AV monitoring unit 36 and thus cause the respective AV monitoring interval to be broken off.

It has already been mentioned above that the V-sense classification unit 48 is adapted to classify ventricular sense events occurring outside a respective AV monitoring interval as ventricular extrasystoles (VES) or premature ventricular contraction (PVC) and in such a case to output a control signal by way of the control line 82.

If in contrast the ventricular sense event is classified by the V-sense classification unit 48 as a regular ventricular sense event which does not occur in a running AV interval, the V-sense classification unit 48 delivers a signal to the VA interval timer 42 by way of the control line 86. To suppress the delivery of an output signal of the V-sense classification unit 48 by way of the control line 86 during a running AV interval the V-sense classification unit 48 is connected to the AV interval timer 34 by way of a control line 85. Thus the VA interval timer 42 is started by an output signal of the V-sense classification unit 48 if, after an atrial signal which occurs in a PMT protection interval and which starts the AV monitoring interval, a ventricular signal occurs in the AV monitoring interval.

If, in a defined period of time prior to the arrival of a signal by way of the control line 86, a signal characterizing an atrial sense event has arrived by way of the control line 76.4 at the interval timer 42, which occurs in a PMT protection interval, characterized by a signal which is applied to the VA interval timer 42 by way of the control line 62.1, the VA interval timer 42 starts a VA interval and at the same time delivers a control signal by way of a control line 88 to the AA interval timer 32, the control signal resetting the latter. The VA interval which is started in that way can be reset by a further control signal which arrives within that VA interval, by way of the control line 76.4. At the same time the AA interval timer 32 is also started again.

To sum up the prerequisite for starting of a VA interval by the VA interval timer 42 is that in a defined relationship in respect of time firstly a signal characterizing an atrial sense event arrives at the VA interval timer 42 by way of the control line 76.4 while at the same time a control signal characterizing the course of a PMT protection interval is applied by way of the control line 62.1 at the VA interval timer 42 and a signal characterizing a natural ventricular sense event follows by way of the control line 86.

If the VA interval in the VA interval timer 42 expires without a preceding reset, then at the end of the VA interval a control signal is outputted by way of the control line 66 to the atrial stimulation control unit 44, which thereupon by way of a signal by way of the control line 20 starts the atrial stimulation unit 24 and triggers atrial stimulation.

The AA interval timer 32 is also started by a signal characterizing an atrial sense event, by way of the control line 76.1. If, within that AA interval, no further control signal arrives by way of the control line 76.1 or by way of the control line 88, which reset the AA interval timer and trigger a fresh AA interval, the AA interval timer 32 delivers a control signal by way of the control line 64 to the atrial stimulation control unit 44 which thereupon triggers the atrial stimulation unit 24. In the case of successful stimulation and correspondingly successful capture control, the atrial stimulation control unit 44 delivers by way of the control return line 70 to the AA interval timer 32 a signal which also causes resetting of the respectively running AA interval and starting of a new AA interval.

FIG. 1 does not show a variant, which is also in accordance with the invention, of the control unit 18 for a VDD cardiac pacemaker which does not include any atrial stimulation unit. In such a VDD pacemaker therefore the atrial stimulation unit 24, the atrial stimulation control unit 44, the VA interval timer and possibly also the AA interval timer can be omitted. A VDD pacemaker however generally also has both an AA timer 32 and also a VA interval timer 42, the respective output signals of which, as described above, serve for starting the AV interval timer 34 by way of the control lines 64.1 and 66.1 respectively.

FIG. 1 also does not show a variant in which the respective pacemaker includes a statistics unit. In such a case the V-sense classification unit is preferably connected to the statistics unit so that the occurrence of ventricular extrasystoles classified by the V-sense classification unit or premature ventricular contractions can be detected and processed with the statistics unit.

Besides that variant, all alternative configurations of the control unit 18 which produce the same performance as that described hereinbefore are also included in the scope of protection of the invention.

Figure 2:
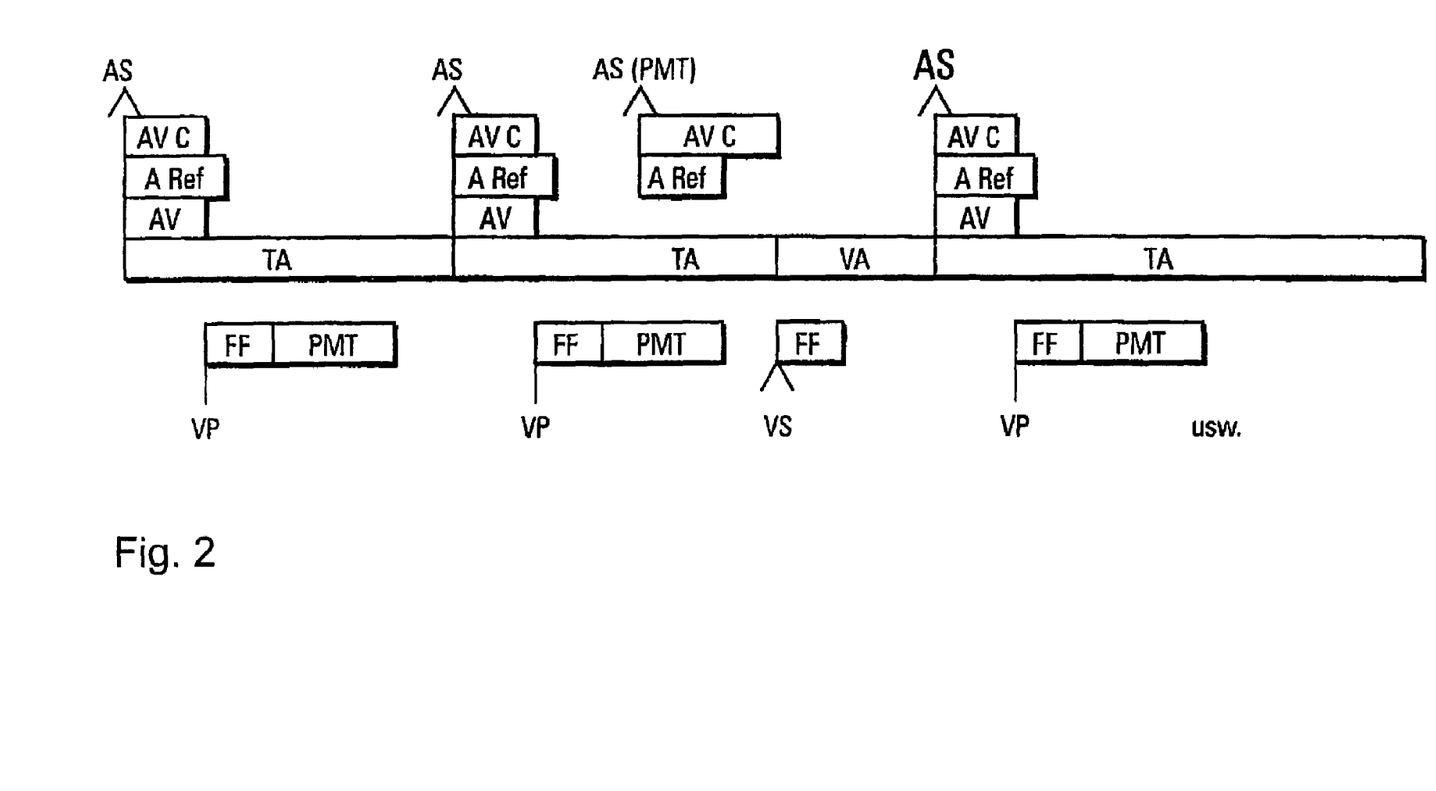
FIG. 2 shows a timing of a cardiac pacemaker, implemented with the control shown in FIG. 1.

In order to clearly show that performance, FIG. 2 illustrates by way of example the configuration of the various intervals in dependence on correspondingly atrial sense and ventricular sense and stimulation events. Atrial sense events are denoted by AS, ventricular sense events are denoted by VS and ventricular stimulation events are denoted by VP. The AV monitoring unit is identified by AVC, the atrial refractory time by ARef and the AV interval by AV. The remote field protection interval is also identified by FF and the PMT protection interval is identified by PMT.

A timing like that shown in FIG. 2 is implemented by the control unit 18 of FIG. 1.

What is claimed is:

1. A dual-chamber cardiac pacemaker for a heart, comprising:
   an atrial detection unit adapted to detect electrical signals in the atrium of the heart as atrial sense events;
   a ventricular detection unit adapted to detect electrical signals of a ventricle of the heart as ventricular sense events;
   a stimulation unit adapted at least to trigger the delivery of electrical pulses to the ventricle as ventricular stimulation events; and
   a control unit connected to the atrial and the ventricular detection units and the stimulation unit and adapted to control triggering of the delivery of pulses in dependence on the atrial detection unit and the ventricular detection unit such that pulse delivery to the ventricle is triggered after the expiry of an AV time after detection of an atrial sense event if prior to expiry of the AV time no ventricular sense event is detected by the ventricular detection unit,
   wherein the control unit is further adapted to divide ventricular sense events into at least two categories, of which a first category concerns ventricular sense events to be associated with natural stimulus conduction from the atrium to the ventricle and a second category concerns ventricular sense events to be associated with ventricular extrasystoles or premature ventricular contractions (PVC) and
   wherein control of the cardiac pacemaker is differentiated in accordance with whether a ventricular sense event is or is not associated with the first category, characterized in that for the control of triggering of pulse delivery an AV monitoring interval is provided in such a way that the AV monitoring interval is triggered by each atrial sense event which is outside an atrial refractory time, wherein the cardiac pacemaker is adapted to associate ventricular events occurring within the AV monitoring interval to the first category, and
   wherein the cardiac pacemaker is adapted, in the case of ventricular sense events which occur within the AV monitoring interval and outside the AV time, to start a VA interval which is prematurely concluded if an atrial sense event occurs prior to the expiry thereof.

2. The cardiac pacemaker of claim 1, wherein the cardiac pacemaker is adapted with an atrial sense event to start an AA interval which is prematurely concluded if within the AV monitoring interval a ventricular sense event occurs and the VA interval is started or if an atrial sense event occurs prior to expiry of the AA interval.

3. The cardiac pacemaker of claim 2, wherein it is the control unit that is adapted with an atrial sense event to start the AA interval which is prematurely concluded if within the AV monitoring interval a ventricular sense event occurs and the VA interval is started or if an atrial sense event occurs prior to expiry of the AA interval.

4. The cardiac pacemaker of claim 3, further comprising:
an atrial stimulation unit adapted to trigger the delivery of electrical pulses to the atrium as atrial stimulation events,
wherein the cardiac pacemaker is adapted to trigger the delivery of an atrial stimulation pulse with the expiry of the VA interval or the AA interval if the VA interval or the AA interval are not prematurely concluded.

5. The cardiac pacemaker of claim 4, wherein it is the control unit that is adapted to trigger the delivery of an atrial stimulation pulse with the expiry of the VA interval or the AA interval if the VA interval or the AA interval are not prematurely concluded.

6. The cardiac pacemaker of claim 2, further comprising:
an atrial stimulation unit adapted to trigger the delivery of electrical pulses to the atrium as atrial stimulation events,
wherein the cardiac pacemaker is adapted to trigger the delivery of an atrial stimulation pulse with the expiry of the VA interval or the AA interval if the VA interval or the AA interval are not prematurely concluded.

7. The cardiac pacemaker of claim 6, wherein it is the control unit that is adapted to trigger the delivery of an atrial stimulation pulse with the expiry of the VA interval or the AA interval if the VA interval or the AA interval are not prematurely concluded.

8. The cardiac pacemaker of claim 1, further comprising:
an atrial stimulation unit adapted to trigger the delivery of electrical pulses to the atrium as atrial stimulation events,
wherein the cardiac pacemaker is adapted to trigger the delivery of an atrial stimulation pulse with the expiry of the VA interval or the AA interval if the VA interval or the AA interval are not prematurely concluded.

9. The cardiac pacemaker of claim 8, wherein
it is the control unit that is adapted to trigger the delivery of an atrial stimulation pulse with the expiry of the VA interval or the AA interval if the VA interval or the AA interval are not prematurely concluded.

10. The cardiac pacemaker of claim 1, wherein a remote field protection interval and a PMT protection interval are provided for the control of triggering of pulse delivery in such a way that the remote field protection interval is triggered by each ventricular stimulation event and by each ventricular sense event detected by the ventricular detection unit, wherein the remote field protection interval has a time duration such that an atrial sense event as a result of a remote field effect of a ventricular event occurs in the remote field protection interval and wherein the effect of the remote field protection interval is that atrial events detected by the atrial detection unit during the remote field protection interval remain disregarded for triggering of pulse delivery by the stimulation unit so that triggering of pulse delivery does not occur after an atrial sense event as a consequence of cross-sensing or remote field detection of ventricular events, and in such a way that the PMT protection interval is triggered by each ventricular stimulation event and by each ventricular sense event detected by the ventricular detection unit if said ventricular event was detected outside a predetermined AV time or outside an AV monitoring interval, wherein if the PMT protection interval were triggered, it adjoins the respective remote field protection interval and prolongs same and wherein the effect of the PMT protection interval is that atrial events detected by the atrial detection unit during the PMT protection interval remain disregarded for triggering of pulse delivery by the stimulation unit so that triggering of pulse delivery as a consequence of an atrial event which goes back to retrograde stimulus conduction from the ventricle to the atrium does not occur.

11. The cardiac pacemaker of claim 10, wherein the control unit is adapted to trigger the AV monitoring interval after each atrial sense event which is outside the atrial refractory time and outside the remote field protection interval.

12. The cardiac pacemaker of claim 1, wherein it is the control unit that is adapted to start a VA interval which is prematurely concluded if an atrial sense event occurs prior to the expiry thereof.

13. The cardiac pacemaker of claim 12, wherein the cardiac pacemaker is adapted with an atrial sense event to start an AA interval which is prematurely concluded if within the AV monitoring interval a ventricular sense event occurs and the VA interval is started or if an atrial sense event occurs prior to expiry of the AA interval.

14. The cardiac pacemaker of claim 13, wherein it is the control unit that is adapted with an atrial sense event to start the AA interval which is prematurely concluded if within the AV monitoring interval a ventricular sense event occurs and the VA interval is started or if an atrial sense event occurs prior to expiry of the AA interval.

15. The cardiac pacemaker of claim 14, further comprising:
an atrial stimulation unit adapted to trigger the delivery of electrical pulses to the atrium as atrial stimulation events,
wherein the cardiac pacemaker is adapted to trigger the delivery of an atrial stimulation pulse with the expiry of the VA interval or the AA interval if the VA interval or the AA interval are not prematurely concluded.

16. The cardiac pacemaker of claim 15, wherein it is the control unit that is adapted to trigger the delivery of an atrial stimulation pulse with the expiry of the VA interval or the AA interval if the VA interval or the AA interval are not prematurely concluded.

17. The cardiac pacemaker of claim 13, further comprising:
an atrial stimulation unit adapted to trigger the delivery of electrical pulses to the atrium as atrial stimulation events,
wherein the cardiac pacemaker is adapted to trigger the delivery of an atrial stimulation pulse with the expiry of the VA interval or the AA interval if the VA interval or the AA interval are not prematurely concluded.

18. The cardiac pacemaker of claim 17, wherein it is the control unit that is adapted to trigger the delivery of an atrial stimulation pulse with the expiry of the VA interval or the AA interval if the VA interval or the AA interval are not prematurely concluded.

19. The cardiac pacemaker of claim 12, further comprising:
    an atrial stimulation unit adapted to trigger the delivery of electrical pulses to the atrium as atrial stimulation events,
    wherein the cardiac pacemaker is adapted to trigger the delivery of an atrial stimulation pulse with the expiry of the VA interval or the AA interval if the VA interval or the AA interval are not prematurely concluded.

20. The cardiac pacemaker of claim 19, wherein it is the control unit that is adapted to trigger the delivery of an atrial stimulation pulse with the expiry of the VA interval or the AA interval if the VA interval or the AA interval are not prematurely concluded.

* * * * *